United States Patent [19]

Allen et al.

[11] Patent Number: 4,578,394
[45] Date of Patent: Mar. 25, 1986

[54] CHOLINERGIC FUNCTION INCREASING 3-[N-(PYRIDYL) CARBAMOYL]-1,4-DIHYDROPYRIDINES

[75] Inventors: Richard C. Allen, Flemington; Richard C. Effland; Joseph T. Klein, both of Bridgewater, all of N.J.

[73] Assignee: Hoechst-Roussel Pharmaceuticals Incorporated, Somerville, N.J.

[21] Appl. No.: 680,036

[22] Filed: Dec. 10, 1984

[51] Int. Cl.⁴ .................. C07D 401/12; A61K 31/455
[52] U.S. Cl. ..................................... 514/332; 546/262
[58] Field of Search .......................... 546/262; 514/332

[56] References Cited
PUBLICATIONS

Bodor, N. et al, "Improved Delivery through Biological Membranes. 13 . . . " J. Med. Chem., 26, 528-534 (1983).
Bodor, N. et al, "Improved Delivery through Biological Membranes. 11 . . . " J. Med. Chem., 26, 313-318 (1983).

Primary Examiner—Henry R. Jiles
Assistant Examiner—Dale A. Bjorkman
Attorney, Agent, or Firm—Jerome Rosenstock

[57] ABSTRACT

This invention relates to 1,4 dihydropyridines having the following formula

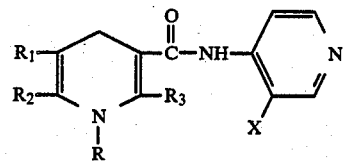

wherein R is loweralkyl or Arloweralkyl; $R_1$, $R_2$ and $R_3$ may be the same or different and are hydrogen, loweralkyl or halogen; X is hydrogen, $NH_2$,

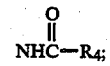

and $R_4$ is hydrogen or loweralkyl. The compounds of this invention display utility in the treatment of Alzheimer's disease and related cognitive disorders characterized by centrally deficient cholinergic function.

13 Claims, No Drawings

CHOLINERGIC FUNCTION INCREASING 3-[N-(PYRIDYL) CARBAMOYL]-1,4-DIHYDROPYRIDINES

This invention relates to compounds of the formula

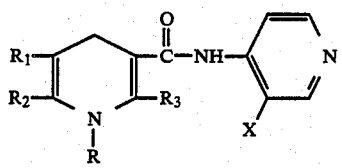
(I)

where R is loweralkyl or Arloweralkyl; $R_1$, $R_2$ and $R_3$ may be the same or different and are hydrogen, loweralkyl or halogen; X is hydrogen, $NH_2$,

and $R_4$ is hydrogen or loweralkyl.

To the best of our knowledge the compounds of the present invention have not been described or suggested.

Throughout the specification and appended claims, a given chemical formula or name shall encompass all stereoisomers thereof where such isomers exist.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc; the term "Arloweralkyl" refers to a monovalent substituent which consists of an aryl group, e.g., phenyl, o-toluyl, m-methoxyphenyl, etc. linked through a lower alkylene group having its free valence bond from a carbon of the lower alkylene group, and having a formula of

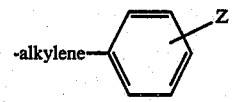

where Z is hydrogen, halogen, loweralkyl, loweralkoxy, $CF_3$, and $NH_2$; the term "alkylene" refers to a bivalent radical of the lower branched or unbranched alkyl group it is derived from having valence bonds from two terminal carbons thereof, e.g. ethylene ($-CH_2CH_2-$), propylene ($-CH_2CH_2CH_2-$), isopropylene

etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.; and the term "halogen" refers to a member of the family consisting of fluorine, chlorine, bromine and iodine.

The compounds of the present invention are prepared in the following manner. The substituents X, R, $R_1$, $R_2$, $R_3$, and $R_4$ are as defined above unless indicated otherwise. A susbtituted nicotinic acid of formula II is selected.

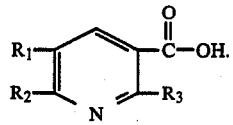
(II)

Such acids are commercially available or are readily synthesized using conventional techniques well known in the art.

Acid II is treated with a halide of the formula R—Hal (III), where Hal is a halogen selected from Cl, Br and I, to form a compound

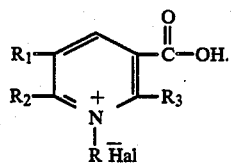
(IV)

Compound IV is typically obtained by reacting compounds II and III under nucleophilic reaction conditions, e.g. in the presence of an inert solvent such as methanol, ethanol, acetone, etc., at a temperature of 60° to 80° C. for 2 to 24 hours.

Compound IV is then converted to an acid halide of the formula

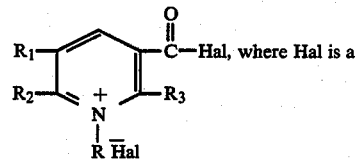
(V)

halide, in a conventional manner, e.g. by treatment with inorganic halides such as $PCl_3$, $PBr_3$, $PCl_5$, $SOCl_2$, etc. in an inert solvent, e.g. dichloromethane, benzene, at a temperature of 50° to 80° C., for 2 to 6 hours. Compound V in turn is then reacted with an aminopyridine of the formula

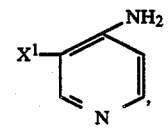
(VI)

where $X^1$
defined above as hydrogen or $NO_2$, to form an intermediate of the invention having the formula

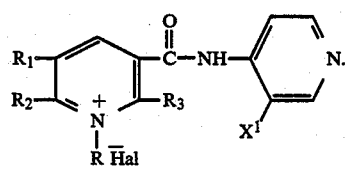
(VII)

Such amino pyridines VI are well known in the art and may be prepared using conventional methods. Compound V is reacted with Compound VI under conventional nucleophilic reaction conditions, typically in the presence of a base, e.g. NaHCO$_3$, Na$_2$CO$_3$, triethylamine, etc. and an inert solvent, e.g. dimethylformamide, pyridine, benzene, etc. at a temperature of 50° to 100° C. for 2 to 24 hours to form Compound VII.

Compound VII is then reduced under conditions where the quaternary pyridinium ring is reduced more readily than the aminopyridyl group to form Compound I. Generally this reduction is carried out in a conventional manner with such reducing agents as for example, sodium dithionite in the presence of base, e.g. NaHCO$_3$, at a temperature of 0° to 25° C. for 1 to 6 hours in a biphasic aqueous media with an organic solvent such as dichloromethane, ethyl acetate, ether, etc.

All other starting materials shown above are either known compounds or easily prepared by routine methods known to the art from readily available materials.

The 1,4-dihydropyridines of the present invention are useful in the treatment of various memory dysfunctions characterized by decreased cholinergic function, such as in Alzheimer's disease.

This utility is demonstrated by the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution of suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
6-chloro-1-methyl-3-[N-(4-pyridyl)carbamoyl]-1,4-dihydropyridine;

3-[N-(3-amino-4-pyridyl)carbamoyl]-1-methyl-1,4-dihydropyridine;

3-[N-(3-acetamido-4-pyridyl)carbamoyl]-1,4-dihydropyridine;

1,2,6-trimethyl-3-[N-(4-pyridyl)carbamoyl]-1,4-dihydropyridine;

5-chloro-1-methyl-3-[N-(4-pyridyl)carbamoyl]-1,4-dihydropyridine;

1-benzyl-3-[N-(4-pyridyl)carbamoyl]-1,4-dihydropyridine;

2-chloro-1-methyl-3-[N-(4-pyridyl)carbamoyl]-1,4-dihydropyridine; and 1,5-dimethyl-3-[N-(4-pyridyl)carbamoyl]-1,4-dihydropyridine.

The following example is given for illustrative purposes and is not to be considered as limiting the invention disclosed herein.

EXAMPLE

1-Methyl-3-[N-(4-pyridyl)carbamoyl]-1,4-dihydropyridine

A mixture of trigonelline hydrochloride (5 g, 29 mmole) and thionyl chloride (25 ml., 40 g, 0.34 mole) was stirred at 85°–90° C. for three hours and then was evaporated to a solid (5.5 g, d 175°–177° C.). To a solution of the resulting acid chloride in dimethylformamide (70 ml), warmed to 80° C., was slowly added a solution of 4-aminopyridine (3.8 g, 40 mmole) in 25 ml dimethylformamide. After stirring twenty hours at 75° C. the reaction mixture was cooled with an ice bath and the precipitated product was collected and recrystallized from ethanol-methanol) (10:1) to give 5 g (70%) of a solid. To a solution of the resulting 1-methyl-3-[N-pyridyl)carbamoyl]pyridinium chloride (3.6 g, 13 mmole) in 200 ml deaerated water were added sodium bicarbonate (6.3 g, 76 mmole) and 200 ml deaerated dichloromethane. The reaction mixture was cooled with an ice bath and sodium dithionite (8.8 g, 50 mmole) was added over a five minute period. After stirring cold for six hours, the mixture was separated and the aqueous layer was extracted with dichloromethane. The organic extract was dried (anhydrous MgSO4), filtered and evaporated to 2.3 g (85%) of a solid of 1-methyl-3-[N-(4-pyridyl)carbamoyl]-1,4-dihydropyridine, mp 120°–122° C.

ANALYSIS: Calculated for $C_{12}H_{13}N_3O$: 66.95%C, 6.09%H, 19.53%N. Found: 66.97C, 6.21%H, 19.18%N.

We claim:

1. A compound having the formula

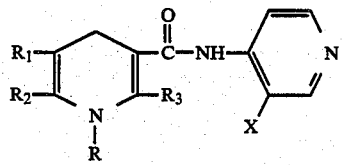

where R is loweralkyl or Arloweralkyl having a formula of

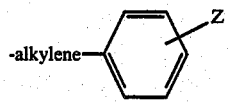

where Z is hydrogen, halogen, loweralkyl, loweralkoxy, CF3, or NH2; R1, R2 and R3 may be the same or different and is hydrogen, loweralkyl or halogen; X is hydrogen, NH2, or

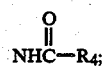

and R4 is hydrogen or loweralkyl.

2. The compound as defined in claim 1 which is 1-methyl-3-[N-(4-pyridyl)carbamoyl]-1,4-dihydropyridine.

3. The compound as defined in claim 1 which is 6-chloro-1-methyl-3-[N-(4-pyridyl)carbamoyl]-1,4-dihydropyridine.

4. The compound as defined in claim 1 which is 3-[N-(3-amino-4-pyridyl)carbamoyl]-1-methyl-1,4-dihydropyridine.

5. A compound having the formula

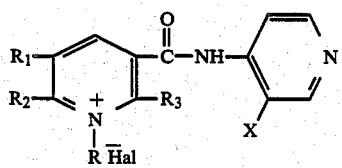

wherein R is loweralkyl or Arloweralkyl having a formula of

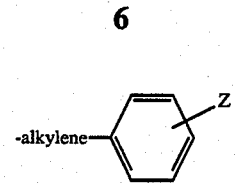

where Z is hydrogen, halogen, loweralkyl, loweralkoxy, CF3, or NH2; R1, R2 may be the same or different and is hydrogen, loweralkyl or halogen; X is hydrogen, NH2;

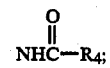

or NO2; R4 is hydrogen or loweralkyl; and Hal is a halogen selected from Cl, Br and I.

6. A composition for increasing the cholinergic function in a mammal which comprises an effective amount for increasing the cholinergic function in a mammal of a compound having the formula

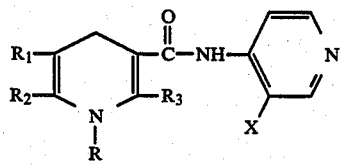

where R is loweralkyl or Arloweralkyl having a formula of

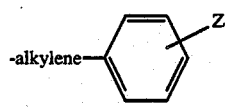

where Z is hydrogen, halogen, loweralkyl, loweralkoxy, CF3, or NH2; R1, R2 and R3 may be the same or different and is hydrogen, loweralkyl or halogen; X is hydrogen, NH2, or

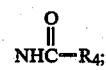

and R4 is hydrogen or loweralkyl; and an inert carrier.

7. The composition as defined in claim 6 which comprises 1-methyl-3-[N-(4-pyridyl)carbamoyl]-1,4-dihydropyridine.

8. The composition as defined in claim 6 which comprises 6-chloro-1-methyl-3-[N-(4-pyridyl)carbamoyl]-1,4-dihydropyridine.

9. The composition as defined in claim 6 which comprises 3-[N-(3-amino-4-pyridyl)carbamoyl]-1-methyl-1,4-dihydropyridine.

10. A method of increasing the cholinergic function in a mammal which comprises administering to the mammal an effective cholinergic function increasing amount of a compound having the formula

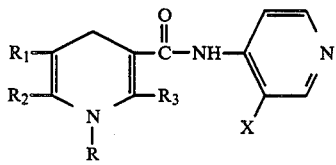

where R is loweralkyl or Arloweralkyl having a formula of

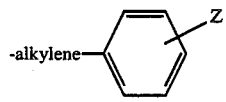

where Z is hydrogen, halogen, loweralkyl, loweralkoxy, $CF_3$, or $NH_2$; $R_1$, $R_2$ and $R_3$ may be the same or different and is hydrogen, loweralkyl or halogen; X is hydrogen, $NH_2$, or

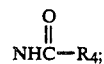

and $R_4$ is hydrogen or loweralkyl.

11. The method as defined in claim 10 wherein said compound comprises 1-methyl-3-[N-(4-pyridyl)carbamoyl]-1,4-dihydropyridine.

12. The method as defined in claim 10 wherein said compound comprises 6-chloro-1-methyl-3-[N-(4-pyridyl)carbamoyl]-1,4-dihydropyridine.

13. The method as defined in claim 10 wherein said compound comprises 3-[N-(3-amino-4-pyridyl)carbamoyl]-1-methyl-1,4-dihydropyridine.

* * * * *